US012731688B2

(12) United States Patent
Khandakar et al.

(10) Patent No.: US 12,731,688 B2
(45) Date of Patent: Sep. 8, 2026

(54) MACHINE LEARNING MODEL FOR STRATIFICATION OF EARLY DIABETIC FOOT COMPLICATION USING THERMOGRAM IMAGES

(71) Applicants: Qatar Foundation for Education, Science and Community Development, Doha (QA); Qatar University, Doha (QA); WEILL CORNELL MEDICAL COLLEGE IN QATAR, Doha (QA)

(72) Inventors: Amith Khandakar, Doha (QA); Muhammad E. H. Chowdhury, Doha (QA); Mamun Bin Ibne Reaz, Doha (QA); Sawal Hamid Md Ali, Doha (QA); Serkan Kiranyaz, Doha (QA); Tawsifur Rahman, Doha (QA); Rashad Alfkey, Doha (QA); Ahmad Ashrif A. Bakar, Doha (QA); Rayaz A. Malik, Doha (QA); Mohamed Arselene Ayari, Doha (QA); Moajjem Hossain Chowdhury, Doha (QA); Kanchon Kanti Podder, Doha (QA); Md Anwarul Hasan, Doha (QA)

(73) Assignees: Qatar Foundation for Education, Science and Community Development, Doha (QA); Weill Cornell Medical College in Qatar, Doha (QA)

( * ) Notice: Subject to any disclaimer, the term of this patent is extended or adjusted under 35 U.S.C. 154(b) by 246 days.

(21) Appl. No.: 18/378,479

(22) Filed: Oct. 10, 2023

(65) Prior Publication Data

US 2024/0120097 A1 Apr. 11, 2024

Related U.S. Application Data

(60) Provisional application No. 63/414,645, filed on Oct. 10, 2022.

(51) Int. Cl.
*G16H 50/20* (2018.01)
*A61B 5/00* (2006.01)
(Continued)

(52) U.S. Cl.
CPC .......... *G16H 50/20* (2018.01); *A61B 5/0013* (2013.01); *G06T 7/0012* (2013.01); *G16H 50/30* (2018.01);
(Continued)

(58) Field of Classification Search
CPC ......... A61B 5/015; A61B 5/447; A61B 5/445; A61B 5/0077; A61B 5/7275;
(Continued)

(56) References Cited

U.S. PATENT DOCUMENTS 10,993,625 B1 * 5/2021 Steikuniene ......... A61B 5/6898
2013/0261494 A1 * 10/2013 Bloom ................. A61B 5/0075
600/549
2018/0132730 A1 * 5/2018 Linders .................. A61B 5/447

OTHER PUBLICATIONS

Kiranyaz, Serkan, et al. "Self-organized operational neural networks with generative neurons." Neural Networks 140 (2021): 294-308. (Year: 2021).*

(Continued)

*Primary Examiner* — Courtney Joan Nelson
(74) *Attorney, Agent, or Firm* — K&L Gates LLP

(57) ABSTRACT

A machine learning model for stratification of early diabetic foot complication using thermogram images is provided that is operable to predictively diagnose a risk for diabetic foot ulceration formation via receiving a thermogram of a foot; identifying, via a machine learning model, a risk factor of diabetic foot ulceration on the foot; and outputting, from the machine learning model, the risk factor as a diagnosis.

9 Claims, 7 Drawing Sheets

(51) Int. Cl.
*G06T 7/00* (2017.01)
*G16H 50/30* (2018.01)

(52) U.S. Cl.
CPC .............. *G06T 2207/10048* (2013.01); *G06T 2207/30196* (2013.01)

(58) Field of Classification Search
CPC . A61B 5/0008; A61B 2576/02; A61B 5/6829; A61B 2562/0271; A61B 5/441; A61B 5/7264; A61B 5/4842; A61B 5/6898; A61B 5/7267; A61B 5/0013; A61B 5/01; A61B 5/00; A61B 5/1074; G16H 50/30; G16H 50/20; G16H 30/40; G06T 2207/20084; G06T 7/0012; G06T 2207/20081; G06T 2207/30088; G06T 2207/30004; G06T 2207/1004; G06T 2207/30196
See application file for complete search history.

(56) References Cited

OTHER PUBLICATIONS

S. Mohanty, S. Goel, R. Nijhawan and S. Gupta, "Identification of Diabetic Foot Ulcer in Images using Machine Learning, " 2021 19th OITS International Conference on Information Technology (OCIT), Bhubaneswar, India, 2021, pp. 221-225, doi: 10.1109/OCIT53463.2021.00052 (Year: 2021).*
Fraiwan, L., AlKhodari, M., Ninan, J. et al. Diabetic foot ulcer mobile detection system using smart phone thermal camera: a feasibility study. BioMed Eng OnLine 16, 117 (2017). https://doi.org/10.1186/s12938-017-0408-x (Year: 2017).*
Sandler, Mark, et al. "Mobilenetv2: Inverted residuals and linear bottlenecks." Proceedings of the IEEE conference on computer vision and pattern recognition. 2018 (Year: 2018).*
Schiborn, C., Schulze, M.B. Precision prognostics for the development of complications in diabetes. Diabetologia 65, 1867-1882 (2022). https://doi.org/10.1007/s00125-022-05731-4 (Year: 2022).*
Ogurtsova, et al.; "IDF Diabetes Atlas: Global estimates for the prevalence of diabetes for 2015 and 2040"; ScienceDirect; vol. 128; Jun. 2017; (8 pages).
Sims Jr., et al.; "Risk factors in the diabetic foot. Recognition and management"; PubMed; 1988; (1 page).
Iversen, et al; "History of foot ulcer increases mortality among individuals with diabetes: ten-year follow-up of the Nord-Trøndelag Health Study, Norway"; PubMed; Dec. 2009; (2 pages).
Reyzelman, et al.; "Continuous Temperature-Monitoring Socks for Home Use in Patients With Diabetes: Observational Study"; PubMed; Dec. 2018; (2 pages).
Armstrong, et al.; "Diabetic Foot Ulcers and Their Recurrence"; PubMed; Jun. 2017; (1 page).
Ananian, et al.; "A multicenter, randomized, single-blind trial comparing the efficacy of viable cryopreserved placental membrane to human fibroblast-derived dermal substitute for the treatment of chronic diabetic foot ulcers"; PubMed; May 2018; (2 pages).
Frykberg, et al.; "Feasibility and Efficacy of a Smart Mat Technology to Predict Development of Diabetic Plantar Ulcers"; PubMed; Jul. 2017; (2 pages).
Nagase; "The Impact of Diabetic Foot Problems on Health-related Quality of Life of People with Diabetes"; School of Public Health—University of Alberta; 2016; (105 pages).
Van Doremalen, et al.; "Infrared 3D Thermography for Inflammation Detection in Diabetic Foot Disease: A Proof of Concept"; Journal of Diabetes Science and Technology; vol. 14; 2019; (9 pages).
Crisologo, et al.; "Remote home monitoring to identify and prevent diabetic foot ulceration"; PubMed; Nov. 2017; (1 page).
Hernandez-Contreras, et al.; "Narrative review: Diabetic foot and infrared thermography"; ScienceDirect; vol. 78; Sep. 2016; (8 pages).
Ring; "Thermal imaging today and its relevance to diabetes"; PubMed; Jul. 2010; (2 pages).
Chan, et al.; "Contact thermography of painful diabetic neuropathic foot"; PubMed; Oct. 1991; (1 page).
Nagase, et al.; "Variations of plantar thermographic patterns in normal controls and non-ulcer diabetic patients: novel classification using angiosome concept"; PubMed; Jul. 2011; (1 page).
Mori, et al.; "Morphological pattern classification system for plantar thermography of patients with diabetes"; PubMed; Sep. 2013; (2 pages).
Jones; "A reappraisal of the use of infrared thermal image analysis in medicine"; PubMed; Dec. 1998; (1 page).
Kaabouch, et al.; "Asymmetry analysis based on genetic algorithms for the prediction of foot ulcers"; ResearchGate; Jan. 2009; (38 pages).
Kaabouch, et al.; "Enhancement of the asymmetry-based overlapping analysis through features extraction"; ResearchGate; Jan. 2011; (12 pages).
Liu, et al.; "Automatic detection of diabetic foot complications with infrared thermography by asymmetric analysis"; PubMed; Feb. 2015; (1 page).
Hernandez-Contreras, et al.; "Automatic classification of thermal patterns in diabetic foot based on morphological pattern spectrum"; ScienceDirect; vol. 73; Nov. 2015; (7 pages).
Hernandez-Contreras, et al.; "A quantitative index for classification of plantar thermal changes in the diabetic foot"; ScienceDirect; vol. 81; Mar. 2017; (7 pages).
Hernandez-Contreras, et al.; "Statistical Approximation of Plantar Temperature Distribution on Diabetic Subjects Based on Beta Mixture Model"; ResearchGate; Mar. 2019; (5 pages).
Cruz-Vega, et al.; "Deep Learning Classification for Diabetic Foot Thermograms"; PubMed; Mar. 2020; (2 pages).
Hernandez-Contreras, et al.; "Plantar Thermogram Database for the Study of Diabetic Foot Complications"; ResearchGate; Nov. 2019; (30 pages).
Maldonado, et al.; "Automatic detection of risk zones in diabetic foot soles by processing thermographic images taken in an uncontrolled environment"; ScienceDirect; vol. 105; Mar. 2020; (55 pages).
Saminathan, et al. "Computer aided detection of diabetic foot ulcer using asymmetry analysis of texture and temperature features"; ScienceDirect; vol. 105; Mar. 2020; (7 pages).
Adam, et al.; "Automated characterization of diabetic foot using nonlinear features extracted from thermograms"; ScienceDirect; vol. 89; Mar. 2018; (9 pages).
Gururajarao, et al.; "Chapter 4—Infrared Thermography and Soft Computing for Diabetic Foot Assessment"; ScienceDirect; 2019; (35 pages).
Etehadtavakol, et al.; "Rapid extraction of the hottest or coldest regions of medical thermographic images"; Springer Link; vol. 57; Aug. 2018; (7 pages).
Fraiwan, et al.; "Diabetic foot ulcer mobile detection system using smart phone thermal camera: a feasibility study"; PubMed; Oct. 2017; (2 pages).
Alzubaidi, et al.; "DFU_QUTNet: diabetic foot ulcer classification using novel deep convolutional neural network"; ACM Digital Library; Jun. 2020; (6 pages).
Tulloch, et al.; "Machine Learning in the Prevention, Diagnosis and Management of Diabetic Foot Ulcers: A Systematic Review"; IEEE Xplore; vol. 8; Nov. 2020; (6 pages).
Yadav, et al.; "A Review of K-mean Algorithm"; International Journal of Engineering Trends and Technology (IJETT); vol. 4, Issue 7; Jul. 2013; (5 pages).
Khandakar, et al.; "A Novel Machine Learning Approach for Severity Classification of Diabetic Foot Complications Using Thermogram Images"; MDPI; 2022; (23 pages).
Kiranyaz, et al.; "Self-organized Operational Neural Networks with Generative Neurons"; ScienceDirect; vol. 140; Aug. 2021; (28 pages).

(56) References Cited

OTHER PUBLICATIONS

Kiranyaz, et al.; "Operational neural networks"; Neural Computing and Applications; 2020; (24 pages).
Sandler, et al.; "MobileNetV2: Inverted Residuals and Linear Bottlenecks"; IEEE Xplore; 2018; (14 pages).
Huang, et al.; "Densely Connected Convolutional Networks" IEEE Xplore; Jan. 2018; (9 pages).
Boulton; "Diabetic Foot Disease during the COVID-19 Pandemic"; PubMed; Jan. 2021; (2 pages).
Selvaraju, et al.; "Grad-CAM: Visual Explanations from Deep Networks via Gradient-Based Localization"; IEEE; 2017; (4 pages).
Maldonado, et al.; "Automatic detection of risk zones in diabetic foot soles by processing thermographic images taken in an uncontrolled environment"; ScienceDirect; vol. 105; (5 pages).
Hernandez-Contreras, et al.; "Plantar Thermogram Database for the Study of Diabetic Foot Complications"; IEEE Xplore; vol. 7; Nov. 2019; (7 pages).
Hernandez-Contreras, et al.; "A quantitative index for classification of plantar thermal changes in the diabetic foot"; ScienceDirect; vol. 81.

* cited by examiner

Table I. Class wise Performance metrics for the proposed network

| Proposed Network | Class | Accuracy | Precision | Sensitivity | F1-score | Specificity | Inference time (ms) |
|---|---|---|---|---|---|---|---|
| Self-DFUNet | Mild | 98.77 | 96.55 | 98.25 | 97.39 | 98.93 | 6.985 |
| | Moderate | 95.49 | 89.39 | 93.65 | 91.47 | 96.13 | |
| | Severe | 96.72 | 98.33 | 95.16 | 96.72 | 98.33 | |
| | Overall | 95.49 | 95.61 | 95.49 | 95.52 | 97.9 | |

FIG. 4

MACHINE LEARNING MODEL FOR STRATIFICATION OF EARLY DIABETIC FOOT COMPLICATION USING THERMOGRAM IMAGES

CROSS-REFERENCES TO RELATED APPLICATIONS

The present disclosure claims the benefit of U.S. Provisional Patent Application No. 63/414,645 entitled "MACHINE LEARNING MODEL FOR STRATIFICATION OF EARLY DIABETIC FOOT COMPLICATION USING THERMOGRAM IMAGES" and filed on 2022 Oct. 10, which is incorporated herein by reference in its entirety.

TECHNICAL FIELD

The present disclosure relates to a software tools or identifying and quantifying the risk of a patient developing ulcers on the feet due to diabetes based on thermal images of the patient's feet.

SUMMARY

The present disclosure provides new and innovative systems and methods for identifying and quantifying the risk of a patient developing ulcers on the feet due to diabetes based on thermal images of the patient's feet. An artificial intelligence (AI) agent is provided that ingests thermographic images of feet to create a diagnosis for a patient.

Diabetic foot ulceration (DFU) has a major impact on morbidity and mortality in patients with diabetes. Early detection may help to prevent or limit DFU progression and eventually amputation. The application of artificial intelligence (AI) for early detection may have considerable utility for health care professionals, especially in primary care, and for caregivers and patients to keep track of their disease. The critical need for such online solutions, especially for patients at risk of DFU has been highlighted during the COVID-19 pandemic. In the proposed solution, a novel machine learning network-Self-DFUNet can allow severity classification of diabetic foot ulceration from thermogram images captured using Infra-Red (IR) cameras with a smartphone. Optimization of the network has enabled the development of a diagnostic system that outperforms any other proposed non-invasive solution. Furthermore, the described network can be easily deployed on a smartphone-based application.

In various aspects, a method, a system for performing the method, and various goods produced by the method are provided. In various aspects, the method includes: receiving a thermogram of a foot; identifying, via a machine learning model, a risk factor of diabetic foot ulceration on the foot; and outputting, from the machine learning model, the risk factor as a diagnosis.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

BRIEF DESCRIPTION OF THE DRAWINGS

FIG. 4 is a table illustrating of classwise performance metrics, according to embodiments of the present disclosure.

DETAILED DESCRIPTION

Figure 1:
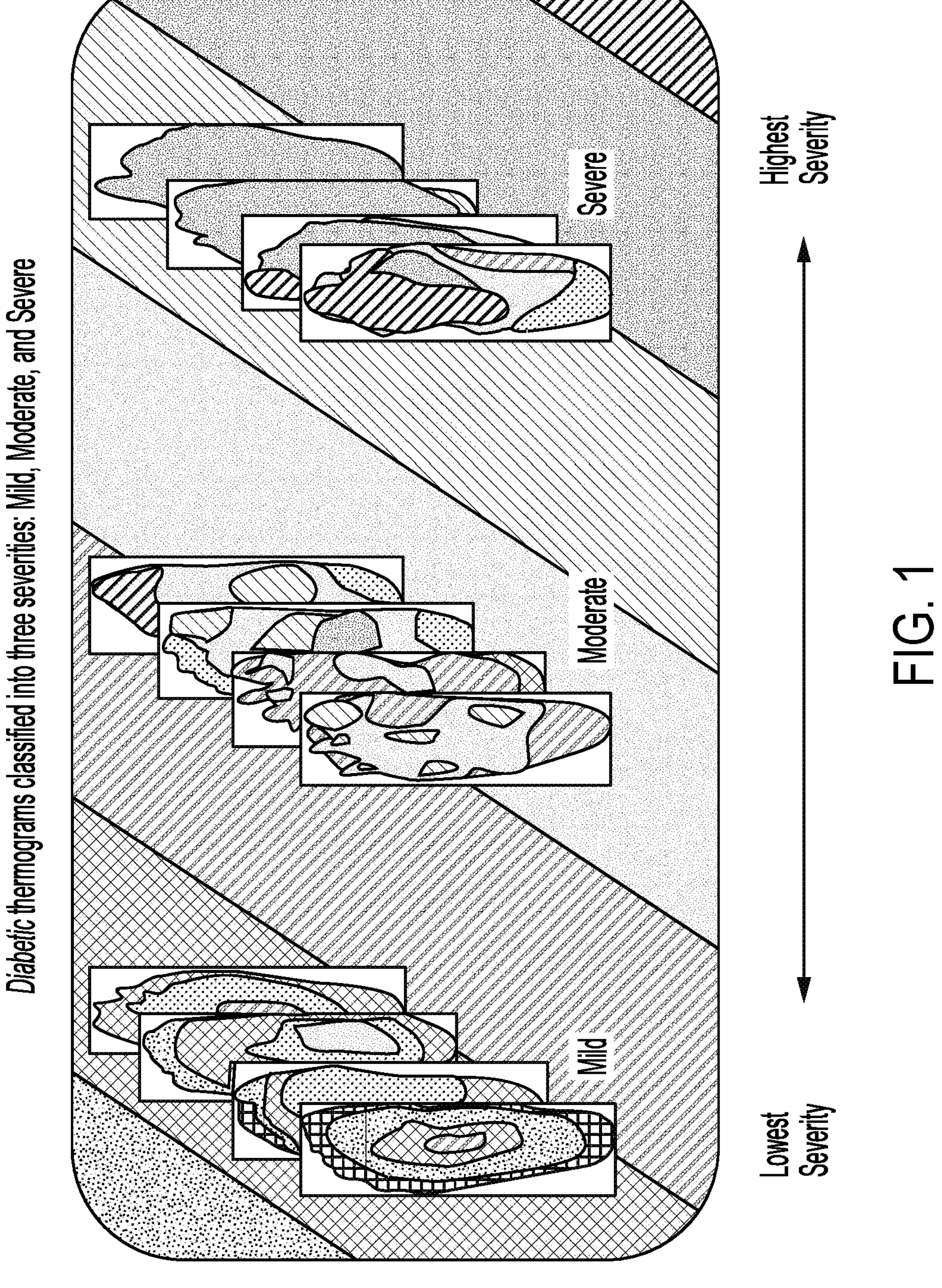
FIG. 1 illustrates example clustering for thermograms, according to embodiments of the present disclosure.

The present disclosure provides new and innovative systems and methods for identifying and quantifying the risk of a patient developing ulcers on the feet due to diabetes based on thermal images of the patient's feet. An artificial intelligence (AI) agent is provided that ingests thermographic images of feet to create a diagnosis for a patient.

The present disclosure provides a real-time solution for severity classification of diabetic patients in relation to their risk of developing Diabetic Foot Ulcer (DFU) from thermogram images. Moreover, the developed light architecture and machine learning model allows deployment via smartphones. Accordingly, the present disclosure provides several novel and innovative contributions, including, but not limited to: the deployment of a severity classification for developing Diabetic Foot ulcers using foot thermogram and a machine learning network that can classify thermograms of diabetic patients into Mild, Moderate and Severe categories.

Diabetes Mellitus (DM) leads to major complications such as heart disease, stroke, renal failure, blindness, and diabetic foot ulceration (DFU) with lower limb amputation. The healing of DFU can be difficult or delayed with an increased risk of infection and amputation. Furthermore, DFU recurs in approximately 40% of patients after the first year and in 60% after three years and leads to amputation in over 1 million diabetic patients annually in the USA. DFU is associated with protracted hospital stay with markedly increased healthcare costs, decreased quality of life, infection, amputation, and death. The detection of patients at risk of DFU may enable timely intervention to prevent foot ulceration, amputation, and death.

Self-care via monitoring for early signs of DFU, may allow timely offloading to prevent skin breakdown and development of an ulcer. Visual inspection has limitations as people with obesity or visual impairment cannot see their site of ulceration. However, recent studies using temperature monitoring have shown that they can predict the development of DFU in 97% of patients. Moreover, studies have also confirmed that patients undergoing continuous foot temperature monitoring had a lower risk of developing a DFU. A temperature difference of 2.22° C. (4° F.) over at least two consecutive days could be used as a threshold for instituting offloading to prevent DFU.

Thermography is a rapid non-invasive imaging technique to quantify changes in tissue temperature in the diabetic foot. Several studies have shown that a characteristic thermal distribution in the infrared image using thermogram-based techniques can identify those at increased risk of DFU. The healthy control group had a specific butterfly pattern compared to a variety of spatial patterns in patients with diabetes. It is possible to assess thermal changes in one foot compared to the contralateral foot, however, if both feet have thermal changes without a butterfly pattern, then one foot cannot act as a reference. Thus, despite a large temperature difference, identical spatial distributions in both feet cannot be used to differentiate feet at risk of DFU. An alternative approach is to calculate the temperature change with respect to the butterfly pattern of a control group.

Whilst it is reasonably straightforward to distinguish the foot thermogram of a control subject with a specific spatial pattern, the distribution of the spatial pattern in a diabetic foot is more challenging, especially as the spatial distribution may change with a temperature rise in the plantar region in diabetic patients. This is where machine learning can help to rapidly extract distinguishable features. Several studies have attempted to extract features to identify the hot region in plantar thermograms, to identify early inflammation and tissue damage, with poor results. Most of these works have been reported on a small private dataset using post-processing techniques, which may not be generalizable on a different dataset, and the real-time applicability and inference time were not reported. Moreover, the performance of these methods was not comparable to machine learning-based techniques and the applicability of the above solutions in smartphone applications was not discussed.

In addition, there is a lack of severity grading for the risk of ulcer development. Expert medical doctors, working in diabetic foot clinics, have shown that foot plantar temperature distribution can help in the early detection of foot ulcer development. Furthermore, the severity classification can help to risk stratify and enable early and targeted interventions to prevent diabetic foot ulcers. The improved performance of a machine learning model can help in early detection from the convenience of the patient's home and reduce the need for face-to face consultations and hence burden on healthcare systems throughout the world.

A pre-trained Convolutional Neural Network (CNN) is used to extract features automatically from the thermogram images, reduce feature dimensionality using principal component analysis (PCA), and classify the thermogram using k-mean clustering to revise the labels. The new labels identified by the unsupervised clusters were fine-tuned by a pool of medical doctors (MDs) according to the severity (Mild, Moderate, and Severe) of Diabetic Foot Ulcers, as seen in FIG. 1. For example, a mild cluster 110, a moderate cluster 120, and a severe cluster 130 of thermograms can be identified from the pool of images.

The experts used their experience of changes in plantar foot temperature distribution as a reference for confirming the severity classification shown the in the clusters. The clusters found by k-mean clustering provided three clearly differentiable sets of thermograms. Plantar foot thermograms with a slightly deviated butterfly pattern were labelled as mild. Those with an abnormal pattern and high-temperature distribution were labelled as moderate as the temperature distribution was still not very high (usually indicated by the red color distribution), but can indicate the possibility of ulcer development in the near future. The third set of plantar foot thermograms had extremely high temperature (indicated by the red color distribution) throughout the foot indicating the possibility of imminent ulcer development and was labelled as severe. Classical machine learning techniques using feature engineering and 2D CNNs with image enhancement techniques were used to develop the best performing classification network.

The present disclosure describes a novel network Self-DFUNet to classify thermogram images of diabetic patients into severity categories based on their probability of developing a DFU. The proposed network is built on Self Organized Operational Neural Network (SelfONN) layers. SelfONN is inspired from the Generalized Operational Perceptrons to address the limitations of Convolutional Neural Networks. Generalized Operational Perceptrons, also known as GOPs, introduce heterogeneous network architectures that resemble real neurons or the mammalian neural system, which is made up of several neuron types with different electrophysiological characteristics. Conventional CNN's employ the traditional "linear" neuron model, but they also impose weight sharing and kernel-wise constrained connections. In contrast, SelfONN uses nodal and pool operators instead of linear weighted sum of CNN. Nodal operators can be exponential, multiplication, harmonic (sinusoid), Gaussian, quadratic function, Laplacian of Gaussian (LoG), Derivative of Gaussian (DoG), Hermitian or any combination of operators. Similarly, the pooling operators can be n-correlation, median, summation, maximum, and any fusion thereof. The nodal operators are approximated using taylor series approximation. To approximate a function f(x) near a point x=a can be expressed in Equation 1.

$$f(x) = f(a) + \frac{f'(a)}{1!}(x-a) + \frac{f''(a)}{2!}(x-a)^2 + \dots + \frac{f^q(a)}{q!}(x-a)^q \quad \text{Equation 1}$$

If $$\frac{f'(a)}{1!}, \frac{f''(a)}{2!}, \frac{f^q(a)}{q!}$$

are considered as $w_1, w_2, w_q$ respectively in the condition x=0, Equation 1 transforms to Equation 2 as:

$$f(x) = b + w_1(x) + w_2(x)^2 + \dots + w_q(x)^q \quad \text{Equation 2}$$

Inverted Bottleneck residual blocks were used in MobileNetV2 architecture and gained superior performance in ImageNet datasets than other comprehensive networks with complex connections. The presently described model, SelfONN based inverted bottleneck residual blocks (Self-IBRes Block) are used instead of conventional CNN based blocks.

Figure 2:
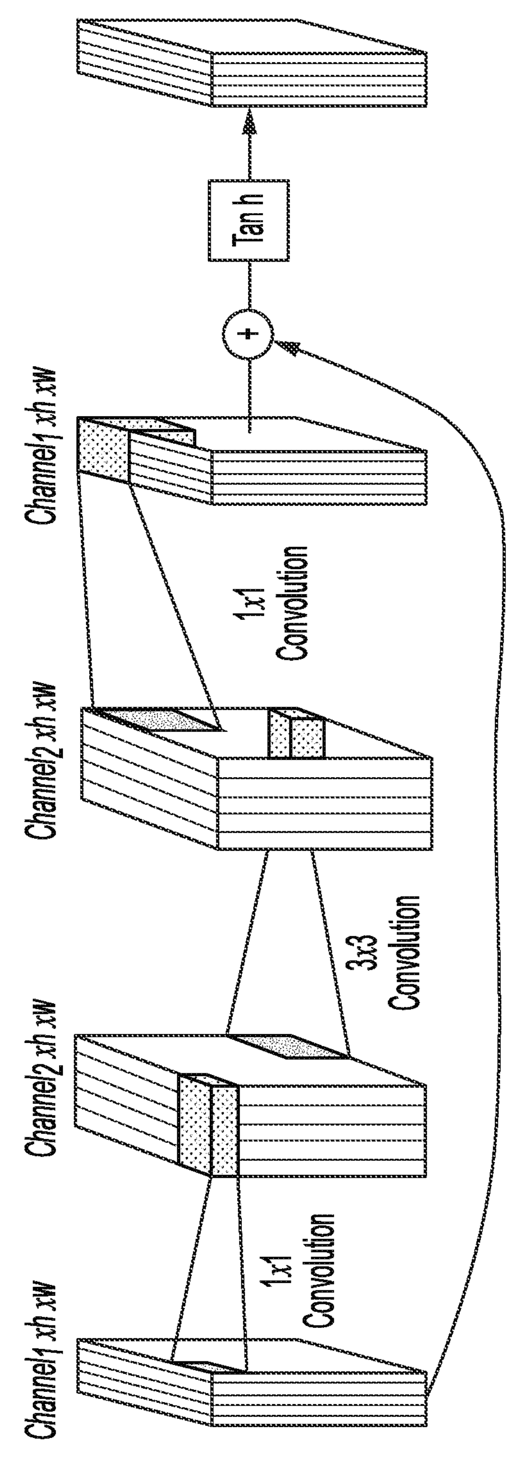
FIG. 2 illustrates an example of the inverted bottleneck residual block, according to embodiments of the present disclosure.

FIG. 2 illustrates an example of the inverted bottleneck residual block 200 using SelfONN layers, according to embodiments of the present disclosure. The depth channel of the input feature is increased by the initial 1×1 convolution, and then a 3×3 convolution is performed by maintaining the same depth. As for the bottleneck properties, the depth channel is reduced by another 1×1 convolution to match the input depth. Each of these SelfONN layers are followed by batch normalization and the residual connection adds the input feature with the convoluted feature map followed by tanh activation.

Figure 3:
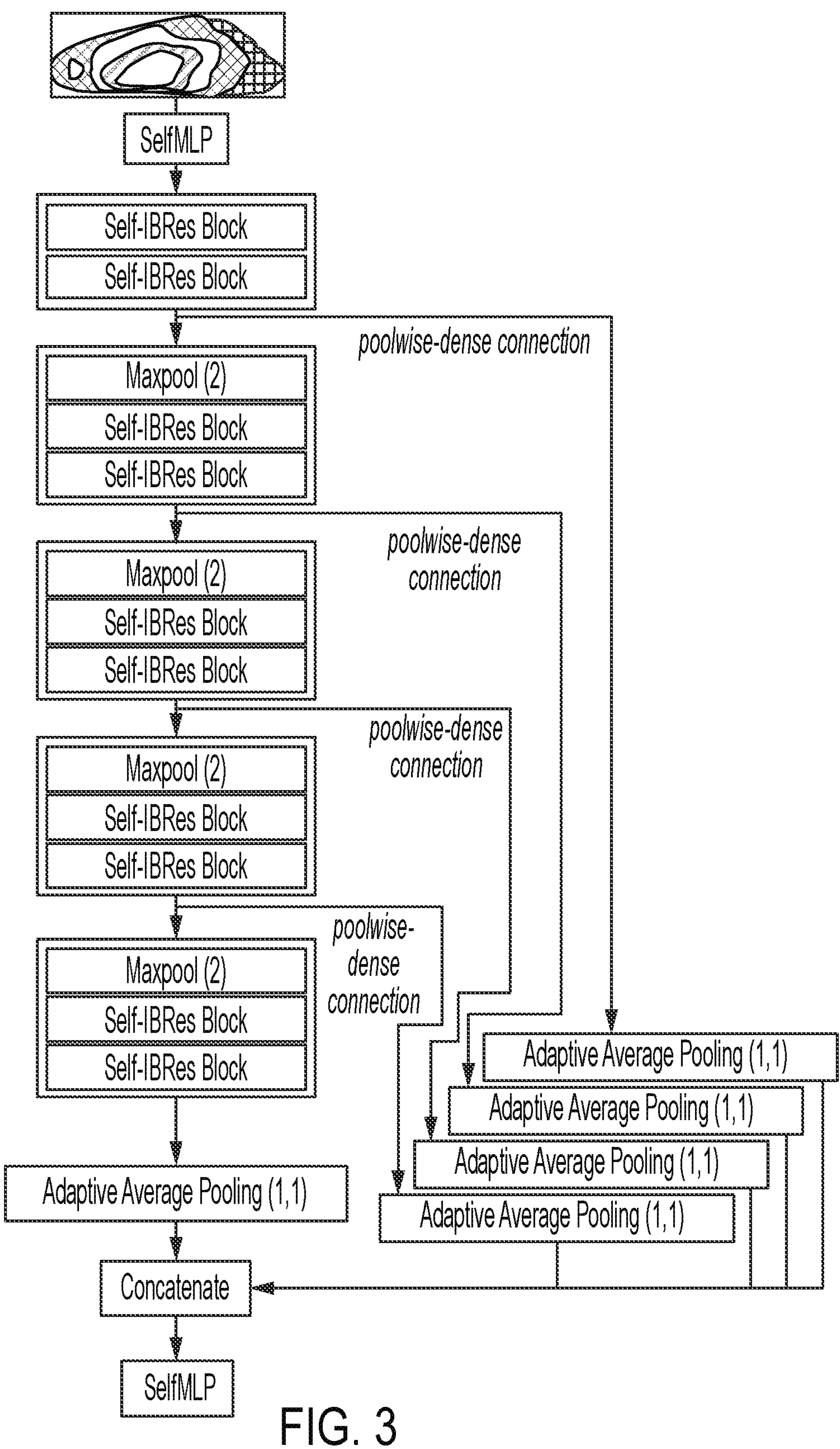
FIG. 3 illustrates an example architecture, according to embodiments of the present disclosure.

FIG. 3 represents the architecture 300 of Self-DFUNet using SelfONN, according to embodiments of the present disclosure. Ten Self-IBResBlocks are used in Self-DFUNet architecture to counter the vanishing gradient problem. The spatial dimension in height×width is reduce as the architecture goes deeper by a stride of 2 SelfONN layer and four maxpooling layers. The preservation of earlier features of the earlier layers is carried out by five adaptive average pooling layers. The adaptive average pooling layers carry average feature in 1×1×channel dimensions. All these average pooled features are concatenated to feed the concentration to the classification layer, which is SelfMLP.

SelfMLP is a counterpart of conventional MLP. SelfMLP is developed based on SelfONN layer, which also uses a composite nodal and pooling operation. Unlike the dense connections used in DenseNet, where the connections are built between succeeding CNN layers, the connections from five Self-IBRes blocks to the concatenation indicate a dense connection that simply flows features to the classification layer. These connections are proposed as poolwise-dense connections. The feature maps from each Self-IBRes block are tanh activated, which means the outputs are in the range of (−1, 1). As a result, the concatenated features coming from each poolwise-dense connection are normalized and prevent the generative neurons of SelfMLP to bias toward any set features of any Self-IBRes block. Accordingly, the advantages of these poolwise-dense connections are feature reuse and strengthened feature propagation. Such connections improve the model performance as the classification layer classifies classes using the features from earlier to deeper layers in a feed-forward manner.

The described network highly accurately categorizes the thermograms of diabetic patients into Mild, Moderate and Severe categories. With FIG. 4 illustrating a table 400 of classwise performance metrics, according to embodiments of the present disclosure.

Figures 5A, 5B, 5C:
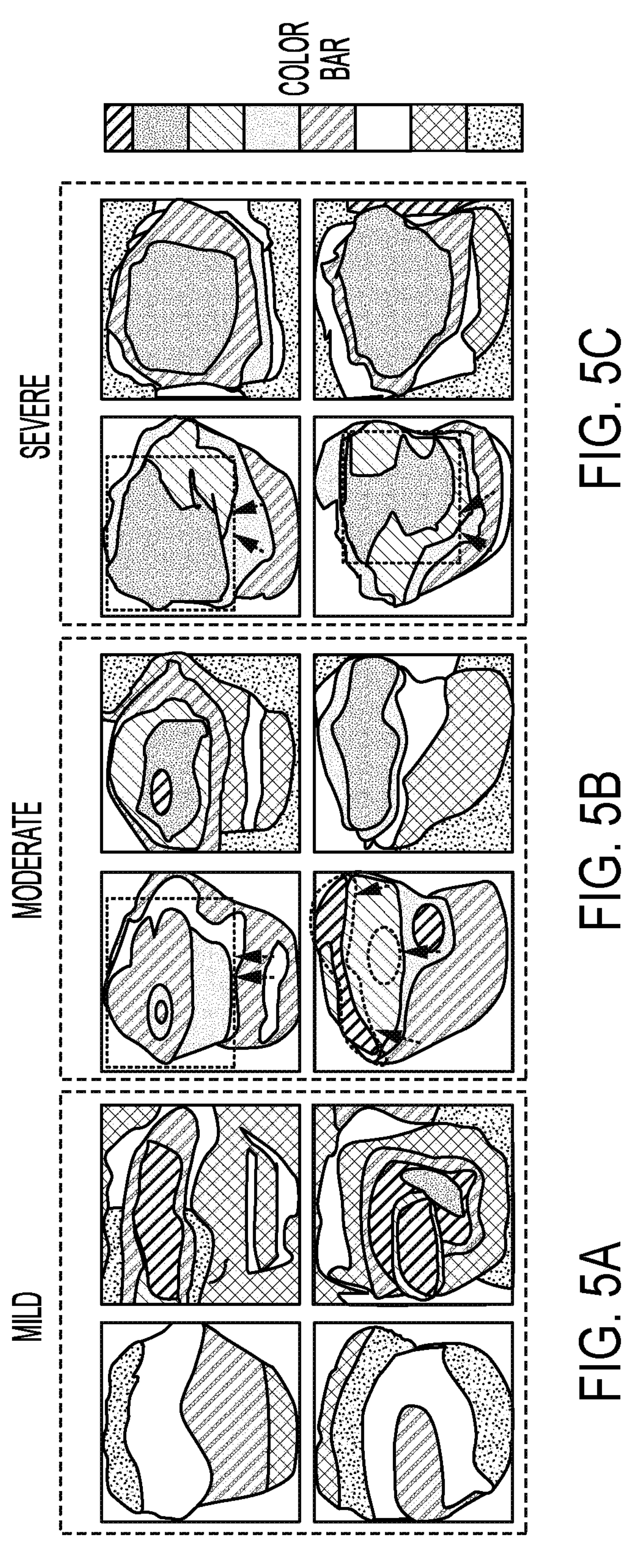
FIG. 5 illustrates an example of thermogram categorization, according to embodiments of the present disclosure.

In addition, the model applies various visualization techniques-GradCAM visualization, to confirm where the network is learning from the thermograms. As can be seen in FIG. 5, the network categorizes the thermograms 510*a-l* into Mild, Moderate and Severe based on the abnormal distribution as shown with arrows in FIG. 5, and also by the extent of the abnormality. The moderate categories have lower abnormality or smaller chunks of hot spots compared to the severe categories where there are large areas of hot spots. The primary contrast is seen in the heatmaps of subjects with Moderate and Severe risk categories. As shown in FIG. 5 Block B, the described network predicts moderate instances based on larger chunks of yellow green spots or smaller red spots in thermogram images. Similarly, severe cases have larger red patches on thermogram images, and Self-DFUNet classifies severe cases based on these indicators. The heatmap produced by GradCAM for each of the three scenarios illustrates how interpretable the proposed model is. By helping users to comprehend the model's learnt characteristics, visualization approaches like this promote user confidence in the model. If it can be determined which area of the foot the network concentrates on for predicting severity, the visualization of model performance in categorizing the severity of DFU may also serve to boost end-user trust.

Figure 6:
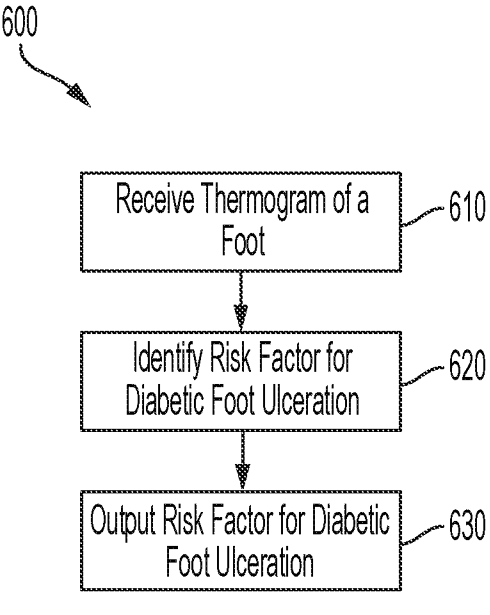
FIG. 6 is a flowchart of an example method for applying an example machine learning model for stratification of early diabetic foot complication using thermogram images, according to embodiments of the present disclosure.

The present disclosure may also be understood with reference to the flowchart of example method 600 shown in FIG. 6. Method 600 begins with block 610, where the model receives a thermogram of a foot. At block 620, the model uses the thermograph to identify a risk factor for diabetic foot ulceration based on the thermogram. At block 630, the model outputs the diagnosed risk factor for DFU formation on the foot.

Based on the diagnosis and the risk factor for DFU formation on the foot, an operator may prescribe or perform a treatment for DFUs on the foot or prescribe or perform a prophylactic treatment against DFUs on the foot.

Figure 7:
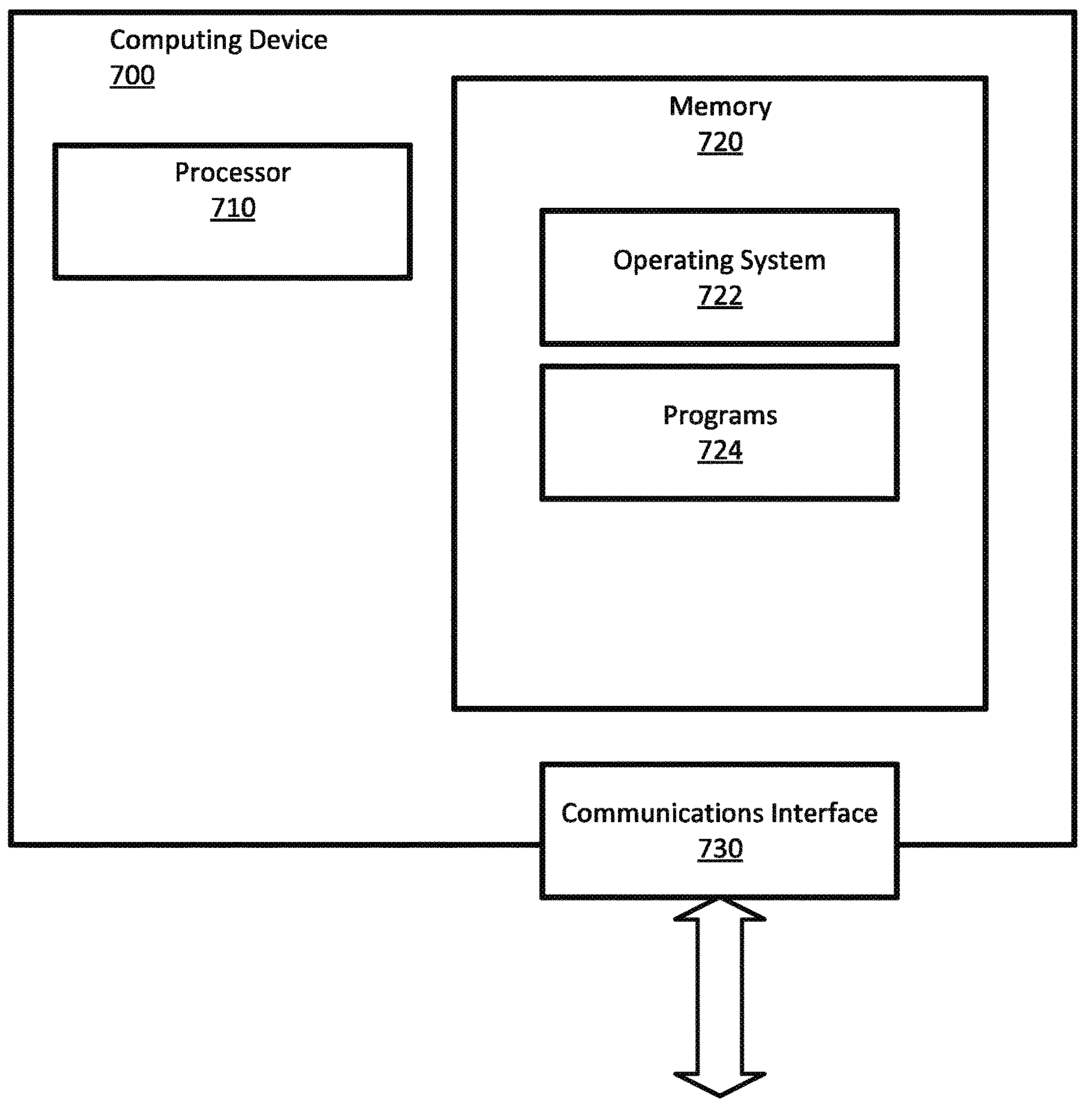
FIG. 7 illustrates a computing device, as may be used to perform the methodologies and provide the machine learning model described herein, according to embodiments of the present disclosure

FIG. 7 illustrates a computing device 700, as may be used to perform the methodologies and provide the machine learning model described herein, according to embodiments of the present disclosure. The computing device 700 may include at least one processor 710, a memory 720, and a communication interface 730.

The processor 710 may be any processing unit capable of performing the operations and procedures described in the present disclosure. In various embodiments, the processor 710 can represent a single processor, multiple processors, a processor with multiple cores, and combinations thereof.

The memory 720 is an apparatus that may be either volatile or non-volatile memory and may include RAM, flash, cache, disk drives, and other computer readable memory storage devices. Although shown as a single entity, the memory 720 may be divided into different memory storage elements such as RAM and one or more hard disk drives. As used herein, the memory 720 is an example of a device that includes computer-readable storage media, and is not to be interpreted as transmission media or signals per se.

As shown, the memory 720 includes various instructions that are executable by the processor 710 to provide an operating system 722 to manage various features of the computing device 700 and one or more programs 724 to provide various functionalities to users of the computing device 700, which include one or more of the features and functionalities described in the present disclosure. One of ordinary skill in the relevant art will recognize that different approaches can be taken in selecting or designing a program 724 to perform the operations described herein, including choice of programming language, the operating system 722 used by the computing device 700, and the architecture of the processor 710 and memory 720. Accordingly, the person of ordinary skill in the relevant art will be able to select or design an appropriate program 724 based on the details provided in the present disclosure.

The communication interface 730 facilitates communications between the computing device 700 and other devices, which may also be computing devices as described in relation to FIG. 7. In various embodiments, the communication interface 730 includes antennas for wireless communications and various wired communication ports. The computing device 700 may also include or be in communication, via the communication interface 730, one or more input devices (e.g., a keyboard, mouse, pen, touch input device, etc.) and one or more output devices (e.g., a display, speakers, a printer, etc.).

Although not explicitly shown in FIG. 7, it should be recognized that the computing device 700 may be connected to one or more public and/or private networks via appropriate network connections via the communication interface 730. It will also be recognized that software instructions may also be loaded into the non-transitory computer readable medium 720 from an appropriate storage medium or via wired or wireless means.

Accordingly, the computing device 700 is an example of a system that includes a processor 710 and a memory 720 that includes instructions that (when executed by the processor 710) perform various embodiments of the present disclosure. Similarly, the memory 720 is an apparatus that includes instructions that when executed by a processor 710 perform various embodiments of the present disclosure.

Certain terms are used throughout the description and claims to refer to particular features or components. As one skilled in the art will appreciate, different persons may refer to the same feature or component by different names. This document does not intend to distinguish between components or features that differ in name but not function.

As used herein, the term "optimize" and variations thereof, is used in a sense understood by data scientists to refer to actions taken for continual improvement of a system relative to a goal. An optimized value will be understood to represent "near-best" value for a given reward framework, which may oscillate around a local maximum or a global maximum for a "best" value or set of values, which may change as the goal changes or as input conditions change. Accordingly, an optimal solution for a first goal at a given time may be suboptimal for a second goal at that time or suboptimal for the first goal at a later time.

As used herein, "about," "approximately" and "substantially" are understood to refer to numbers in a range of the referenced number, for example the range of −10% to +10% of the referenced number, preferably −5% to +5% of the referenced number, more preferably −1% to +1% of the referenced number, most preferably −0.1% to +0.1% of the referenced number.

Furthermore, all numerical ranges herein should be understood to include all integers, whole numbers, or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in the present disclosure, a phrase referring to "at least one of" a list of items refers to any set of those items, including sets with a single member, and every potential combination thereof. For example, when referencing "at least one of A, B, or C" or "at least one of A, B, and C", the phrase is intended to cover the sets of: A, B, C, A-B, B-C, and A-B-C, where the sets may include one or multiple instances of a given member (e.g., A-A, A-A-A, A-A-B, A-A-B-B-C-C-C, etc.) and any ordering thereof. For avoidance of doubt, the phrase "at least one of A, B, and C" shall not be interpreted to mean "at least one of A, at least one of B, and at least one of C".

As used in the present disclosure, the term "determining" encompasses a variety of actions that may include calculating, computing, processing, deriving, investigating, looking up (e.g., via a table, database, or other data structure), ascertaining, receiving (e.g., receiving information), accessing (e.g., accessing data in a memory), retrieving, resolving, selecting, choosing, establishing, and the like.

Without further elaboration, it is believed that one skilled in the art can use the preceding description to use the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

Within the claims, reference to an element in the singular is not intended to mean "one and only one" unless specifically stated as such, but rather as "one or more" or "at least one". Unless specifically stated otherwise, the term "some" refers to one or more. No claim element is to be construed under the provision of 35 U.S.C. § 112(f) unless the element is expressly recited using the phrase "means for" or "step for". All structural and functional equivalents to the elements of the various embodiments described in the present disclosure that are known or come later to be known to those of ordinary skill in the relevant art are expressly incorporated herein by reference and are intended to be encompassed by the claims. Moreover, nothing disclosed in the present disclosure is intended to be dedicated to the public regardless of whether such disclosure is explicitly recited in the claims.

What is claimed is:

1. A method, comprising:

receiving a thermogram of a foot;

identifying, via a machine learning model, a risk factor of diabetic foot complications including diabetic foot ulceration on the foot and at least one of heart disease, stroke, renal failure and blindness, wherein the machine learning model includes poolwise-dense connections in which tanh-activated feature maps from multiple Self Inverted Bottleneck Residual (IBR) blocks are concatenated via adaptive average pooling to feed a Self Multilayer Perceptron (SelfMLP) classification layer, thereby enabling feature reuse, strengthened propagation, and normalized processing across layers to improve accuracy of severity stratification into mild, moderate, or severe categories;

outputting, from the machine learning model, the risk factor as a diagnosis that stratifies the risk into one of the mild, moderate, or severe categories; and applying a prophylactic intervention selected from offloading therapy, pharmacotherapy, or lifestyle modification to prevent progression to diabetic foot ulceration when the risk is stratified as moderate or severe.

2. The method of claim 1, wherein the machine learning model is provided on a mobile phone including a camera with which the thermogram was received.

3. The method of claim 1, wherein the machine learning model is trained on a corpus of thermograms of feet via a unsupervised learning methodology.

4. The method of claim 1, wherein machine learning model is constructed from a plurality of Self Organized Operational Neural Network (SelfONN) layers.

5. A system, comprising:

a processor; and a memory that includes instructions, that when executed by the processor perform operations including:

receiving a thermogram of a foot;

identifying, via a machine learning model, a risk factor of diabetic foot complications including diabetic ulceration on the foot and at least one of heart disease, stroke, renal failure and blindness, wherein the machine learning model includes poolwise-dense connections in which tanh-activated feature maps from multiple Self Inverted Bottleneck Residual (IBR) blocks are concatenated via adaptive average pooling to feed a Self Multilayer Perceptron (SelfMLP) classification layer, thereby enabling feature reuse, strengthened propagation, and normalized processing across layers to improve accuracy of severity stratification into mild, moderate, or severe categories;

outputting, from the machine learning model, the risk factor as a diagnosis that stratifies the risk into one of the mild, moderate, or severe categories; and applying a prophylactic intervention selected from off-loading therapy, pharmacotherapy, or lifestyle modification to prevent progression to diabetic foot ulceration when the risk is stratified as moderate or severe.

6. The system of claim 5, wherein the machine learning model is provided on a mobile phone including a camera with which the thermogram was received.

7. The system of claim 5, wherein the machine learning model is trained on a corpus of thermograms of feet via a unsupervised learning methodology.

8. The system of claim 5, wherein machine learning model is constructed from a plurality of Self Organized Operational Neural Network (SelfONN) layers.

9. A device including computer-readable instructions, that when executed by a processor, perform operations comprising:

receiving a thermogram of a foot;

identifying, via a machine learning model, a risk factor of diabetic foot complications including diabetic ulceration on the foot and at least one of heart disease, stroke, renal failure and blindness, wherein the machine learning model includes poolwise-dense connections in which tanh-activated feature maps from multiple Self Inverted Bottleneck Residual (IBR) blocks are concatenated via adaptive average pooling to feed a Self Multilayer Perceptron (SelfMLP) classification layer, thereby enabling feature reuse, strengthened propagation, and normalized processing across layers to improve accuracy of severity stratification into mild, moderate, or severe categories;

outputting, from the machine learning model, the risk factor as a diagnosis that stratifies the risk into one of the mild, moderate, or severe categories; and applying a prophylactic intervention selected from off-loading therapy, pharmacotherapy, or lifestyle modification to prevent progression to diabetic foot ulceration when the risk is stratified as moderate or severe.

* * * * *